US008147883B1

(12) United States Patent
Msika et al.

(10) Patent No.: US 8,147,883 B1
(45) Date of Patent: Apr. 3, 2012

(54) USE OF A PLANT OIL PRODUCT AS AN AGENT FOR INCREASING THE SYNTHESIS OF SKIN LIPIDS

(75) Inventors: Philippe Msika, Paris (FR); Antoine Piccirilli, Epernon (FR)

(73) Assignee: Laboratoires Expanscience (FR)

( * ) Notice: Subject to any disclaimer, the term of this patent is extended or adjusted under 35 U.S.C. 154(b) by 0 days.

(21) Appl. No.: 10/088,851

(22) PCT Filed: Sep. 20, 2000

(86) PCT No.: PCT/FR00/02600
§ 371 (c)(1),
(2), (4) Date: Mar. 21, 2002

(87) PCT Pub. No.: WO01/21150
PCT Pub. Date: Mar. 29, 2001

(30) Foreign Application Priority Data

Sep. 22, 1999 (FR) ..................................... 99 11844

(51) Int. Cl.
*A61K 36/28* (2006.01)
(52) U.S. Cl. .................... 424/764; 514/859; 514/861
(58) Field of Classification Search .................. 424/757, 424/764, 769, 78.03, 451, 725, 78.02, 439; 514/859, 863, 937, 938, 861, 864
See application file for complete search history.

(56) References Cited

U.S. PATENT DOCUMENTS

| 3,993,756 | A | * | 11/1976 | Kaneda et al. |
| 4,454,159 | A | | 6/1984 | Musher |
| 5,468,490 | A | | 11/1995 | Huber et al. |
| 5,797,555 | A | * | 8/1998 | Shima et al. |
| 5,928,659 | A | * | 7/1999 | Moy |
| 6,582,688 | B1 | | 6/2003 | Broutin et al. |

FOREIGN PATENT DOCUMENTS

| DE | 196 31 792 | | 3/1997 |
| DE | 19652522 A1 | | 6/1998 |
| EP | 0 493 144 | | 7/1992 |
| EP | 0 643 960 | | 3/1995 |
| EP | 0 775 480 | | 5/1997 |
| FR | 2 187 328 | | 1/1974 |
| FR | 2 405 068 | | 5/1979 |
| FR | 2 443 835 | | 7/1980 |
| FR | 2471775 A1 | | 6/1981 |
| FR | 2 648 347 | | 12/1990 |
| FR | 2 653 974 | | 5/1991 |
| FR | 2 678 632 | | 1/1993 |
| FR | 2 692 783 | | 12/1993 |
| FR | 2 694 692 | | 2/1994 |
| FR | 2 724 663 | | 3/1996 |
| FR | 2 762 512 | | 10/1998 |
| FR | 2 778 181 | | 11/1999 |
| GB | 2066071 A | * | 7/1981 |
| JP | 57131716 A | * | 8/1982 |
| JP | 05279242 A | * | 10/1993 |
| WO | WO 94/21764 | | 9/1994 |
| WO | WO 9918913 A2 | * | 4/1999 |
| WO | WO 99/59523 | | 11/1999 |

OTHER PUBLICATIONS

Lamaud, M. E. et al. Pathologie-biologie (1978), 26(5): 269-74. Biochemical modifications of connective tissue induced by the non-saponifiables of avocado and soya-bean oils administered percutaneously in the "Hairless". Abstract.*
Loden, M. et al. The British Journal of Dermatology (Feb. 1996), 134(2): 215-220. Effect of topically applied lipids on surfactant-irritated skin.*
Robert, A. M. et al. G. M. de France, (1975), 82: 62-66. Pharmacologie du tissue connonctif. Action des insaponifiables d'avocat et de soja sur le metabolisme de la matrice intercellulaire.*
Translation of W: Pharmacology of connective tissue. Effect of Avocado and soybean unsaponifiables on metabolism on the intercellular matrix. A. M. Robert et al.*
Milkova T et al. Nahrung (1977); 21(1): 1-6. Study on the chemical nature of sterols contained in Bulgarian sunflower oil.*
Alonso L et al. Journal of the American Oil Chemists' Society (1997); 74(2): 131-135. Determination of mixtures in vegetable oils and milk by fat analysis of sterol fraction by gas chromatography.*
PTO 07-4294. Use of sterol esters s agents for restoring natural oils. Translation of W) 99-18913 ny McElroy Translation Company.*
Ghosh et al. Journal of he American Oil Chemists' Society (1996); 73(10); 1271-1274. Isolation of tocopherol and sterol concentrate from sunflower oil deodorizer distillate.*
Werman MJ et al. (1991); 26(1-2): 1-10. The effect of various avocado oils on skin metabolism collagen.*
Di Nardo et al. Acta Derm Venereol. Jan. 1998;78(1):27-30. Ceramide and cholesterol composition of the skin of patients with atopic dermatitis.*
Ghadially et al., Decreased Epidermal Lipid Synthesis Accounts for Altered Barrier Function in Aged Mice, J Invest Dermatol, vol. 106, pp. 1064-1069 (1996).
Farines et al., Influence of Avocado Oil Processing on the Nature of Some Unsaponifiable Constituents, JAOCS, vol. 72, No. 4, pp. 473-476 (1995).
Ponec et al., Epidermal Growth Factor and Temperature Regulate Keratinocyte Differentiation, Arch Dermatol Res, vol. 289, pp. 317-326 (1997).
Rawlings et al., Effect of Lactic Acid Isomers on Keratinocyte Ceramide Synthesis, Stratum Corneum Lipid Levels and Stratum Corneum Barrier Function, Arch Dermatol Res, vol. 288, pp. 383-390 (1996).
Third Party Observations EPO-DG 2, retrieved Jul. 5, 2010.
European Search Report, EP 06013216, dated Mar. 21, 2007.

* cited by examiner

*Primary Examiner* — Michele Flood
(74) *Attorney, Agent, or Firm* — Lerner, David, Littenberg, Krumholz & Mentlik, LLP

(57) ABSTRACT

The invention concerns the use of at least a vegetable oil product selected among the group consisting of vegetable oil oleic distillates, vegetable oil unsaponifiable matters, vegetable oil furan lipids and mixtures thereof, as agents for increasing skin lipid synthesis, in particular lipids of the epidermal skin barrier, in or for preparing a composition containing a pharmaceutically or dermatologically acceptable medium. The use enables to prevent and/or treat deterioration of the skin barrier (dry skin, skin subjected to actinic radiation, ichthyosis, acne, xerosis, atopic dermatitis, sensitive skin, chafing and reactive skin, itching and the like).

11 Claims, No Drawings

USE OF A PLANT OIL PRODUCT AS AN AGENT FOR INCREASING THE SYNTHESIS OF SKIN LIPIDS

The present invention relates to the use of a plant oil product as an agent for increasing the synthesis of skin lipids, especially the lipids of the epidermal skin barrier, in or for the preparation of a cosmetic, pharmaceutical or dermatological composition. The invention also relates to a method for cosmetic treatment with a cosmetic, pharmaceutical or dermatological composition for increasing the synthesis of skin lipids, especially the lipids of the epidermal skin barrier, and to the use of the plant product as a food additive.

The skin, consists mainly of three layers: the epidermis, the dermis and the hypodermis.

The outermost layer, the epidermis, is characterized by organization into strata corresponding to a state of increasing differentiation of the keratinocytes, from the deepest region (stratum basale) to the outermost region (stratum corneum) within which anuclear elements (corneocytes) are included in a multilamellar extracellular lipid structure, the intercorneocytic cement, responsible for, the skin's water barrier function and for protection against external attack.

The lamellar bodies, or Oddland bodies, secreted by the stratum granulosum, a layer intermediate between the stratum basale and the stratum corneum, contain cholesterol, phospholipids and glucosylceramides and also selective hydrolases. These enzymes convert phospholipids and glucosylceramides into free fatty acids and ceramides which form, with cholesterol and cholesteryl sulfate, the intercellular lamellar bilayers of the stratum corneum. Ceramides participate predominantly in the formation of the barrier formed by the stratum corneum and in regulating water flow by unifying the lamellae. A large reduction in the content of/and the type of ceramide is especially observed in atopic dermatitis (or atopic eczema) or in acne (ceramide 1) and in dry skin and pruritus in the elderly. Cholesteryl sulfate, via a specific sulfatase, is in equilibrium with cholesterol (leaflet-fluidizing agent). They play an important role in corneocyte cohesion and thus in skin desquamation, and also in skin comfort.

An impairment in this skin barrier caused by external attack (UV radiation, wind, cold, detergents, etc.), by the natural and inexorable phenomenon of aging and/or by pathological or nonpathological dysfunctions (sensitive, irritated or reactive skin) is manifested in a disruption in the epidermal homeostasis which it is desirable to able to prevent and/or treat both cosmetically and pharmaceutically and especially dermatologically.

For example, the article by Ruby Ghadially et al., "Decreased Epidermal Lipid Synthesis Accounts for Altered Barrier Function in Aged Mice", The Journal of Investigate Dermatology, vol. 106, no. 5, May 1996, teaches that an impaired skin barrier and also an abnormal content of lipids in an aged mouse epidermis can be explained by an impaired synthesis of the epidermal lipids.

There is thus a need to be able to stimulate the synthesis of the skin lipids, especially the lipids of the epidermal skin barrier, so as to be able in particular to restore the skin barrier function of the epidermis and/or to combat various skin disorders associated with a reduction in the synthesis of skin lipids, especially the lipids of the epidermal skin barrier.

It has now been found, entirely surprisingly and unexpectedly, that the use of certain plant oil products makes it possible advantageously to synthesize skin lipids, especially lipids of the epidermal skin barrier.

One subject of the present invention is thus the use of at least one plant oil product chosen from the group consisting of oil distillates of plant oil, unsaponifiable materials from plant oil, furan lipids of plant oil and mixtures thereof as agents for increasing the synthesis of skin lipids, especially the lipids of the epidermal skin barrier known to those skilled in the art, like those mentioned above, in or for the preparation of a composition containing a cosmetically, pharmaceutically or dermatologically acceptable medium.

In particular, the use according to the invention is characterized in that the skin lipids are chosen, inter alia, from the epidermal lipids of the group consisting of cholesterol, cholesteryl sulfate, ceramides 1 and 2 and mixtures thereof.

Among the plant oils that may be used, mention may be made in particular of sunflower oil, palm oil, palm kernel oil, coconut oil, grapeseed oil, black mustard oil, poppyseed oil, karite butter oil, sweet almond oil, soybean oil, avocado oil, groundnut oil, cotton oil, sesame oil, olive oil, corn oil, cocoa bean oil, castor oil, behen oil, flax oil, rapeseed oil, annatto oil, wheatgerm oil, safflower oil, walnut oil, hazelnut oil and turnipseed oil.

According to the invention, the expression "oil distillate of a plant oil" means a plant oil which has been subjected to a step of concentration of its unsaponifiable material.

The unsaponifiable material is the fraction of a fatty substance which, after prolonged action of an alkaline base, remains insoluble in water and may be extracted with an organic solvent. Five major groups of substances are present in most unsaponifiable materials of plant oils: saturated or unsaturated hydrocarbons, aliphatic or terpenic alcohols, sterols, phytosterols, tocopherols and carotenoid and xanthophyll pigments.

Plant oils whose unsaponifiable material and/or oil distillate are rich in tocopherols and/or phytosterols are particularly preferred for use according to the invention. A person skilled in the art readily understands that the term "rich" refers to tocopherol and phytosterol contents that are respectively above the mean respective contents obtained on consideration of all the plant oils known to those skilled in the art and in particular those mentioned above.

Various methods may be used to concentrate the unsaponifiable material of a plant oil: crystallization under cold conditions, liquid-liquid extraction, molecular distillation.

Molecular distillation is particularly preferred, and is preferably carried out at a temperature of between about 180° C. and about 280° C., maintaining a pressure of between about $10^{-3}$ mmHg and about $10^{-2}$ mmHg and preferably of the order of $10^{-3}$ mmHg. The concentration of unsaponifiable material in the distillate may be up to 60%.

This molecular distillation, as well as any other molecular distillation for the preparation of the plant oil products to be used according to the invention, as described below, is preferably carried out using a device chosen from molecular distillation equipment of centrifugal type and molecular devices of scraped-film type.

Molecular distillation equipment of centrifugal type is known to those skilled in the art. For example, patent application EP-0 493 144 discloses a molecular distillation device of this type. In general, the product to be distilled is spread in a thin film over the heated surface (hot surface) of a conical rotor rotating at high speed. The distillation chamber is placed under vacuum. Under these conditions, evaporation, rather than boiling, takes place, from the hot surface, of the constituents of the unsaponifiable material, the advantage being that the oil and the unsaponifiable material (these products being notoriously fragile) are not degraded during the evaporation.

Molecular distillation devices of scraped-film type, which are also known to those skilled in the art, comprise a distillation chamber which has a rotating scraper, allowing the product to be distilled to be spread continuously over the evaporation surface (hot surface). The product's vapours are condensed by means of a cold finger placed in the centre of the distillation chamber. The peripheral supply and vacuum systems are very similar to those of a centrifugal distillation device (supply pumps, vane vacuum pumps and oil diffusion pumps, etc.). The residues and distillates are recovered in glass round-bottomed flasks by gravitational flow.

According to one particularly preferred embodiment of the present invention, an oil distillate of sunflower oil is used.

Preferably, the oil distillate of sunflower oil is obtained by molecular distillation of a food-grade sunflower oil. The distillation conditions are preferably as follows:

temperature from 230 to 250° C.;
pressure from $10^{-3}$ to $10^{-2}$ mmHg;
degree of distillation of about 5 to 10% by mass.

The degree of distillation may be defined as follows: it is the mass ratio, relative to 100%, of the mass of the distillate to the sum (mass of the distillate+mass of the residue).

The distillate thus obtained, i.e. the oil distillate of sunflower oil, has an unsaponifiable material content of between about 6% and about 10% by weight, the remaining part being composed of sunflower oil triglycerides.

The unsaponifiable material of a plant oil which may be used according to the invention is preferably chosen from the group consisting of the unsaponifiable material of avocado oil and the unsaponifiable material of soybean oil, and mixtures thereof.

Comparison of the unsaponifiable material contents of various plant oils—soybean, cotton, coconut, olive and avocado—shows a very large amount of unsaponifiable material in avocado oil, obtained by extraction according to various known processes. Typically, the contents obtained range from 2 to 7% of unsaponifiable material in avocado oil, compared with 0.5% in coconut oil, 1% in soybean oil and 1% in olive oil.

The higher content of unsaponifiable material in avocado oil compared with the other plant oils such as mentioned above is explained in particular by the presence, in the unsaponifiable material of avocado oil, of constituents which are not generally found in the unsaponifiable material of many other plant oils, such as furan compounds and polyhydroxylated fatty, alcohols, and which, by themselves, represent more than 50% of the unsaponifiable material. The products specific to this unsaponifiable material of avocado oil may be divided into two chemical fractions referred to as "fraction I" and "fraction H". The active compounds for the use according to the invention are present in the H fraction and its precursors. The H fraction appears first on a gas chromatograph of the unsaponifiable material of avocado oil.

As regards the unsaponifiable material of soybean oil, it may be noted that this unsaponifiable material is mainly composed of sterols (40 to 65%) and of tocopherols (≧10%). The main sterols are β-sitosterol (40 to 70% of the total sterols), campesterol (15 to 30% of the total sterols) and stigmasterol (10 to 25% of the total sterols). The tocopherols are present in the form of a mixture of α-tocopherol (5 to 35% of total tocopherols), γ-tocopherol (45 to 70% of the total tocopherols) and δ-tocopherol (10 to 43% of the total tocopherols).

Several processes have been described in the prior art to extract the unsaponifiable material of a plant oil.

Mention may be made in particular of the process for preparing an unsaponifiable material of avocado oil as described and claimed in patent FR-2 678 632 in the name of Laboratoires Pharmascience. This process makes it possible to obtain an unsaponifiable material of avocado oil which are rich in H fraction, compared with the conventional processes for preparing the unsaponifiable material of avocado.

Thus, the unsaponifiable material of avocado oil used according to the invention may be obtained from the fresh fruit, but, preferably, the unsaponifiable material of avocado is prepared from fruit that has been heat-treated beforehand, prior to extracting the oil and saponifying it, as described in patent FR-2 678 632.

This heat treatment consists of a controlled drying of the fruit, which is preferably fresh, for at least four hours, advantageously at least 10 hours, preferably between about 24 and about 48 hours, at a temperature preferably of at least about 80° C. and preferably between about 80° C. and about 120° C.

Mention may also be made of the process for preparing the unsaponifiable material of soybean oil, obtained from, a concentrate of unsaponifiable material of soybean oil. The said concentrate of unsaponifiable material is prepared by molecular distillation according to a process such as the one described for lupin oil in patent application FR-A 762 512, but adapted to soybean oil. In this process, the soybean oil is distilled in a molecular distillation device of centrifugal type or of scraped-film type, at a temperature of between about 210° C. and 250° C. and under a high vacuum of between 0.01 and 0.001 millimeters of mercury (i.e. 0.13 to 1.3 Pa). The distillate obtained has an unsaponifiable material content of between 5% and 30% by weight and thus constitutes a concentrate of unsaponifiable material of soybean oil. This concentrate is then saponified according to a conventional saponification process, in the presence of ethanolic potassium hydroxide. The mixture obtained is extracted with dichloroethane in a counter current column. Finally, the solvent is removed from the solvent phase by passing it through a falling-film evaporator in order to recover the unsaponifiable material of soybean.

According to one preferred embodiment of the present invention, the unsaponifiable material of a plant oil is a mixture of unsaponifiable material of avocado oil and of soybean oil, the weight ratio of unsaponifiable material of avocado oil to the unsaponifiable material of soybean oil being between about 0.1 and about 9 and preferably between about 0.25 and about 0.6.

In particular, it is advantageously possible to use the mixture of unsaponifiable materials of avocado oil and of soybean oil as sold by the company Laboratoires Pharmascience under the name "Piascledine 300®" which consists of a mixture of 33.3% by weight of unsaponifiable material of avocado and 66.6% by weight of unsaponifiable material of soybean, relative to the total weight of the mixture (the remaining 0.1% consisting of colloidal silica and butylhydroxytoluene).

According to the invention, the expression "furan lipids of a plant oil" means compounds comprising a linear $C_{11}$-$C_{19}$ hydrocarbon-based main chain, which is saturated or comprises one or more ethylenic or acetylenic unsaturations, and a 2-furyl group at one of its ends. Among the furan lipids of a plant oil which may be used according to the invention, the ones most particularly preferred are the furan lipids of avocado. This is because avocado comprises specific lipids of furan type, the main component of which is a linoleic furan:

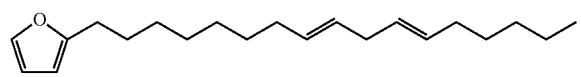

furan compound H7

The furan derivatives of avocado oil have been described in particular in Farines, M. et al, 1995, J. of Am. Oil Chem. Soc. 72, 473. It is nowadays well established that the presence of these furan compounds in the leaves or fruit depends not only on the variety (the varieties Hass and Fuerte being richest in furan compounds) but also on the method for obtaining the oil or another plant extract of avocado (hexane or ethanolic extract of avocado leaves).

Specifically, it is known that these furan lipids are metabolites of compounds that are initially present in the fruit and leaves and which, under the effect of heat, dehydrate and cyclize to give furan derivatives.

For example, linoleic furan is derived from the thermal conversion of the following precursor:

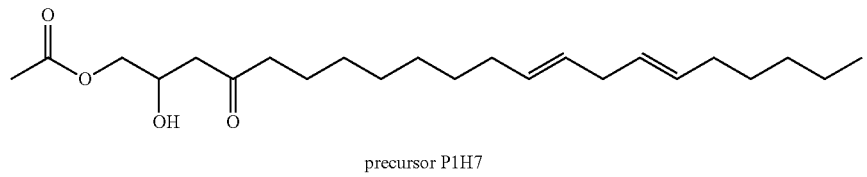

precursor P1H7

According to the invention, the expression "furan lipids of avocado" in particular means the components corresponding to the formula:

in which R is a linear $C_{11}$-$C_{19}$, preferably $C_{13}$-$C_{17}$, hydrocarbon-based chain which is saturated or comprises one or more ethylenic or acetylenic unsaturations.

The known processes for obtaining these specific compounds from avocado fruit or from avocado fruit oil come down to either preparative chromatography or industrial processes for obtaining these furan lipids as a mixture with the other unsaponifiable compounds of avocado, with a maximum content of furan-containing lipids which is at best between 50% and about 65% by weight only.

A novel process for preparing these furan lipids of avocado was the subject of a patent application filed this very day. It consists essentially of a process for selectively extracting the furan lipids of avocado, characterized in that it comprises the steps consisting in preparing an unsaponifiable material of avocado and then in subjecting the unsaponifiable material of avocado to a step of molecular distillation using temperature means regulated for a temperature of between 100° C. and 160° C. and pressure means regulated for a pressure of between $10^{-3}$ mmHg and $5 \times 10^{-2}$ mmHg.

This molecular distillation step using specific temperature and pressure conditions constitutes an essential characteristic of this process, in combination with the prior step of preparing the unsaponifiable material already described above.

According to the invention, the plant oil product as described above is used in a proportion of between about 0.01% and 100% by weight and preferably between about 0.5% and about 10% by weight relative to the total weight of the composition.

The cosmetically, pharmaceutically or dermatologically acceptable medium for the use according to the invention may be any medium that is suitable for the presentation forms known to those skilled in the art, for topical, oral, enteral or parenteral administration.

In particular, this medium may be an oily solution, a water-in-oil emulsion, an oil-in-water emulsion, a microemulsion, an oily gel, an anhydrous gel, or a dispersion of vesicles, microcapsules or microparticles.

The composition for the use according to the invention is preferably suitable for administration by topical application.

The advantageous effect of increasing the synthesis of the skin lipids, especially the lipids of the epidermal skin barrier, makes, it possible to prevent and/or treat, in other words allows the treatment of, impairments of the skin barrier formed mainly by the epidermal layers of the stratum corneum and the stratum granulosum as explained above.

Thus, the use according to the invention is characterized in that the composition is intended for treating dry skin and skin that has been subjected to actinic radiation, especially UV radiation, such as solar radiation or radiation from a UV lamp, for example during an artificial tanning session.

The use according to the invention is also characterized in that the composition is intended for treating ichthyosis, acne, xerosis, atopic dermatitis (or atopic eczema), skin disorders associated with a reduction in the content of skin lipids, especially the lipids of the epidermal skin barrier, and disorders of corneocyte cohesion and of desquamation of the skin, sensitive, irritated and reactive skin, and pruritus.

A subject of the present invention is also a method for cosmetic treatment disorders associated with aging of the skin, neighboring mucous membranes and/or integuments, characterized in that a composition containing at least one plant oil product in a cosmetically acceptable medium as described above is applied to the skin, neighboring mucous membranes and/or integuments.

A subject of the invention is also a method for cosmetic treatment of disorders associated with drying of the skin, neighboring mucous membranes and/or integuments, characterized in that a composition containing at least one plant oil product in a cosmetically acceptable medium as described above is applied to the skin, neighboring mucous membranes and/or integuments.

A subject of the invention is also a method for cosmetic treatment of disorders of the skin, neighboring mucous membranes and/or integuments, resulting from an exposure to actinic radiation, especially UV radiation, characterized in that a composition containing at least one plant oil product in a cosmetically acceptable medium as described above is applied to the skin and/or integuments.

According to one preferred embodiment of these cosmetic treatment methods, the plant oil product is present in the composition in a proportion of between about 0.01% and 100% by weight and preferably between about 0.5% and about 10% by weight relative to the total weight of the composition.

A subject of the present invention is also a cosmetic, pharmaceutical or dermatological composition for increasing the synthesis of skin lipids, especially the lipids of the epidermal skin barrier, characterized in that it comprises at least one plant oil product in a cosmetically, pharmaceutically or dermatologically acceptable medium, as described above.

Preferably, this composition is characterized in that the plant oil product is present in the composition in a proportion of between about 0.01% and 100% by weight and preferably between about 0.5% and about 10% by weight relative to the total weight of the composition.

Finally, another subject of the invention is the use of at least one plant oil product, as described above, as an additive in a food for humans and/or animals.

This food use is preferably characterized in that the plant oil product is present in the food in a proportion of between about 0.1% and about 20% by weight relative to the total weight of the food.

The examples which follow are intended to illustrate the present invention and should not in any way be interpreted as possibly limiting its scope.

Unless otherwise specified, the percentages indicated in the examples below are percentages by weight.

EXAMPLE 1

Preparation of Plant Oil Products and their Use According to the Invention in the Form of Oil-in-Water Emulsions The following compositions 1.1 to 1.3 and the placebo composition were each prepared in the following way:

The constituent components of the aqueous phase (water and glycerol) are placed in a water bath at 75° C. The components of the fatty phase, except for the Sepigel 305, the Silicone SF 1202 and the plant oil product (prepared below, respectively, under the names "sunflower oil distillate 1", "unsaponifiable materials 1" and "lipids 1"), are placed in a water bath at 75° C. Just before performing the emulsification, the Silicone 1202 and the respective plant oil product are added to the fatty phase. The emulsion is then prepared by turbomixing at low speed by incorporating the fatty phase into the aqueous phase. When the preparation has reached a temperature of 60° C., the Sepigel 305 is added with high-speed turbomixing. The composition is then allowed to cool at rest to room temperature, before being used in the tests described below.

1.1) Composition 1.1: Use of an Oil Distillate of Sunflower Oil

A sunflower oil distillate is prepared by molecular distillation, in a molecular distillation machine of centrifugal type, of a commercial food-grade sunflower oil. The distillation conditions are as follows:

temperature 220° C.;
pressure of $10^{-3}$ mmHg;
degree of distillation: 6/7% by mass
feed rate: 18 kg/h The distillate obtained, sunflower oil distillate, has a content of unsaponifiable materials of about 6.2% by weight, the remaining portion being composed of sunflower oil triglycerides. The oil distillate thus obtained is referred to as "sunflower oil distillate 1".

| Composition 1.1 (INCI formula) | % (by weight) |
| --- | --- |
| Aqueous phase | |
| Water | 67.3 |
| Glycerol | 4 |

-continued

| Composition 1.1 (INCI formula) | % (by weight) |
| --- | --- |
| Fatty phase | |
| Sorbitan tristearate | 1.85 |
| PEG-40 stearate | 3.15 |
| Silicone SF 1202 | 3 |
| cetiol Oe | 1 |
| Petroleum jelly codex | 2.5 |
| Glyceryl stearate | 6 |
| Decyl pentanoate | 3 |
| Sunflower oil distillate 1 | 2 |
| Beeswax | 3 |
| PEG-2 stearate | 1 |
| C12-15 alcohol benzoate | 1 |
| Phenonip | 0.7 |
| Sepigel 305 | 0.3 |
| TOTAL | 100% |

1.2) Composition 1.2: Use of a Mixture of an Unsaponifiable Material from Avocado and from Soybean The mixture of unsaponifiable materials from avocado oil and from soybean oil as sold by the company Laboratoires Pharmascience under the name "Piascledine 300®", which consists of a mixture of 33.3% by weight of unsaponifiable materials from avocado and 66.6% by weight of unsaponifiable materials from soybean, relative to the total weight of the mixture (the remaining 0.1% consisting of colloidal silica and butyl-hydroxytoluene) is used. This mixture is referred to hereinbelow as "unsaponifiable materials 1".

| Composition 1.2 (INCI names) | |
| --- | --- |
| Aqueous phase | |
| Water | 67.3 |
| Glycerol | 4 |
| Fatty phase | |
| Sorbitan tristearate | 1.85 |
| PEG-40 stearate | 3.15 |
| Silicone SF 1202 | 3 |
| Cetiol Oe | 1 |
| Petroleum jelly codex | 2.5 |
| Glyceryl stearate | 6 |
| Decyl pentanoate | 3 |
| Unsaponifiables 1 | 2 |
| Beeswax | 3 |
| PEG-2 stearate | 1 |
| C12-15 alcohol benzoate | 1 |
| Phenonip | 0.7 |
| Sepigel 305 | 0.5 |
| TOTAL | 100% |

1.3) Composition 1.3: Use of Furan-Containing Lipids of Avocado

An unsaponifiable material from avocado is prepared as described in patent FR-2 678 632. Its composition is as follows:

| | |
| --- | --- |
| polyhydroxylated fatty alcohols | 24.3% |
| furan-containing lipids | 55.5% |
| sterols | 3.1% |

-continued

| | | |
|---|---|---|
| squalene | 1.4% | |
| others | 15.7% (1) | |

(1) free fatty acids, hydrocarbons, tocopherols, fatty ketones and heavy pigments This unsaponifiable material is subjected to molecular distillation using the scraped-film molecular distillation machine sold by the company Leybold under the name "KDL4". The distillation conditions are as follows:
- hot-surface temperature: 108° C.
- pressure: $10^{-3}$ mmHg
- rotation speed of the shaft: 240 rpm
- flow rate of unsaponifiable material from avocado: 400 ml/h Yield of distillate: 48.6%
Composition of the distillate:

| | |
|---|---|
| polyhydroxylated fatty alcohols: | n.m. |
| furan-containing lipids | 99.1% |
| sterols | n.m. |
| squalene | n.m. |
| others | 0.9% (1) |

(1) free fatty acids, hydrocarbons and fatty ketones
("n.m.": not measurable, that is to say a content of less than 0.05%)

(1) free fatty acids, hydrocarbons and fatty ketones
("n.m.": not measurable, that is to say a content of less than 0.05%)

This is thus a distillate that is very rich in furan-containing lipids since the content of said lipids exceeds 99%. This distillate is referred to hereinbelow as "lipids 1"

| Composition 1.3 (INCI names) | % (by weight) |
|---|---|
| Aqueous phase | |
| Water | 69 |
| Glycerol | 4 |
| Fatty phase | |
| Sorbitan tristearate | 1.85 |
| PEG-40 stearate | 3.15 |
| Silicone SF 1202 | 3 |
| Cetiol Oe | 1 |
| Petroleum jelly codex | 2.5 |
| Glyceryl stearate | 6 |
| Decyl pentanoate | 3 |
| Lipids 1 | 0.3 |
| Beeswax | 3 |
| PEG-2 stearate | 1 |
| C12-15 alcohol benzoate | 1 |
| Phenonip | 0.7 |
| Sepigel 305 | 0.5 |
| TOTAL | 100% |

1.4) Placebo Composition

| Placebo composition (INCI names) | % (by weight) |
|---|---|
| Aqueous phase | |
| Water | 69.3 |
| Glycerol | 4 |
| Fatty phase | |
| Sorbitan tristearate | 1.85 |
| PEG-40 stearate | 3.15 |
| Silicone SF 1202 | 3 |
| Cetiol Oe | 1 |
| Petroleum jelly codex | 2.5 |
| Glyceryl stearate | 6 |
| Decyl pentanoate | 3 |
| Beeswax | 3 |
| PEG-2 stearate | 1 |
| C12-15 alcohol benzoate | 1 |
| Phenonip | 0.7 |
| Sepigel 305 | 0.5 |
| TOTAL | 100% |

EXAMPLE 2

In Vitro Evaluation of the Effect of Compositions 1.1, 1.2, 1.3 and Placebo on the Metabolism of the Epidermal Lipids in an Organotypical Model of Whole Human Skin in Culture The following abbreviations are used in the text hereinbelow:
EGF: epidermal growth factor;
TLC: thin layer chromatography;
MCF: culture medium for disks of human skin;
MIF: incubation medium for disks of human skin;
PBS: phosphate-buffered saline.

The object of this study is to study the effect of the four compositions 1.1, 1.2, 1.3 and placebo described above on the metabolism of epidermal lipids.

The study is performed in vitro in an organotypical model of whole human skin in culture. Two techniques successively used:
- measurement of the incorporation of acetate radiolabeled with carbon 14 into the neosynthesized epidermal lipids in toto;
- analysis by thin layer chromatography to separate the main classes of neosynthesized radiolabeled epidermal lipids.

The effect of the test products is compared with that observed in the presence of epidermal growth factor (EGF), diluted in the culture medium for the human skin disks, and in the presence of a commercially available cosmetic formulation containing lactic acid. EGF and lactic acid both stimulate, in a known manner, the synthesis of ceramides by the keratinocytes (Ponec M. Gibbs S., Weerheim A., Kempenaar J., Mulder A. and Mommaas A. M.—Epidermal growth factor and temperature regulate keratinocytes differentiation—Arch. Dermatol. Res., 1997, 289, 317-326; and Rawlings A. V., Davies A., Carlomusto M., Pillai S. Ahang K., Kosturbo R., Verdejo P., Feinberg C., Nguyen L. and Chandar P.—Effect of lactic acid isomers on keratinocyte ceramide synthesis, stratum corneum lipid levels and stratum corneum barrier function—Arch. Dermatol. Res., 1996, 288, 383-390).

1) Materials and Method
1.1) Test Products, Reference Products and Reagents

Compositions 1.1, 1.2, 1.3 and placebo were prepared as described above. The EGF was obtained from R&D Systems. The cosmetic formulation containing lactic acid, referred to hereinbelow as "lactic acid", was purchased in the supermarket distribution network.

The solution for rinsing the human skin disks after incubation is PBS buffer: 8 g/l, NaCl; 1.15 g/l $Na_2HPO_4$; 0.2 g/l $KH_2PO_4$; 0.2 g/l KCl; 0.1 g/l $CaCl_2$; 0.1 g/l MgCl2; pH 7.4.

The other reagents, of analytical grade, are obtained from Carlo Erba, Gibco and Sigma, except where otherwise indicated.

1.2) Test System

A fragment of human skin was collected after an abdominal plastic surgery-operation. This was performed on a 24 year old woman (subject I0129). Skin disks 8 mm in diameter were cut out using a sample punch.

The skin disks are placed in gondolas. The gondolas are placed in culture wells containing MCF medium, composed of MEM/M199 medium (3/4, 1/4; v/v) supplemented with penicillin (50 IU/ml), streptomycin (50 µg/ml), sodium bicarbonate (0.2%, w/v) and FCS (2%, v/v).

1.3) Incubation of the Test Products and the Reference Products with the Test System The test products are tested undiluted. They are placed at the center of each human skin disk, in a proportion of 10 mg/cm². The incubation medium for the human skin disks (MIF medium) is composed of MCF medium containing 1 µCi/ml of acetate labeled with carbon 14 (Amersham, specific activity: 57 mCi/mmol).

The EGF is tested at 10 ng/ml in the MIF medium. The lactic acid is used in topical application (10 mg/cm²).

The human skin disks are incubated in the presence of the test products and the reference products for 18 hours at 37° C. in a humid atmosphere containing 5% $CO_2$.

Control skin disks are incubated in parallel in the presence of test products and reference products.

Each experimental condition is performed in quadruplicate.

The following time scale is used:

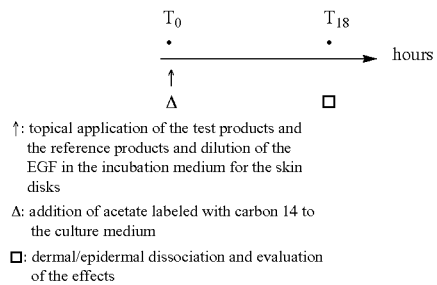

↑: topical application of the test products and the reference products and dilution of the EGF in the incubation medium for the skin disks
Δ: addition of acetate labeled with carbon 14 to the culture medium
□: dermal/epidermal dissociation and evaluation of the effects 1.4) Evaluation of the Effects 1.4.1) Neosynthesis of the Total Epidermal Lipids At the end of the incubation, the human skin disks are rinsed thoroughly with PBS buffer. The epidermis of each skin disk is dissociated from the dermis by means of a controlled heat shock (MilliQ water, 2 min, 62° C.) The epidermises thus dissociated are digested with trypsin (ICN, 1%, w/v) overnight at 37° C. The cell dissociation is facilitated by the action of ultrasound.

The neosynthesized lipids, labeled with carbon 14, are extracted by partition between an organic phase (1/4 methanol/chloroform, v/v) and an aqueous phase (0.25M potassium chloride). The organic phase is evaporated under nitrogen and the residues are taken up in a 2/1 chlotoform/methanol mixture (v/v).

The radioactivity of each sample, corresponding to the amount of acetate incorporated into the neosynthesized lipids, is measured by liquid scintillation.

The results are expressed in cpm/mg of epidermis.

1.4.2) Nature of the Neosynthesized Epidermal Lipids

Starting with the samples of extracted lipids, 20 µl aliquots, corresponding to 3 700 cpm, are placed on silica 60 (Merck) chromatography plates. These plates are developed in three successive solvents:

38/2/10 chloroform/acetone/methanol (v/v/v),
40/5/5 chloroform/acetone/methanol (v/v/v),
36/10/3/1 chloroform/ethyl acetate/ether/methanol (v/v/v/v).

This system makes it possible to separate the cholesteryl sulfate, the cerebrosides, the ceramides, the cholesterol and the tri-+diglycerides. The most polar lipids, referred to hereinbelow as "polar lipids", remain on the base line.

The silica plates are then placed in exposure with films for autoradiography for 15 days (Amersham, Hyperfilm beta max).

The position of the various classes of lipids—polar lipids, cholesteryl sulfate, cerebrosides, ceramides 1 and 2, cholesterol and tri-+diglycerides—is determined using suitable standards.

The radioactivity of the spots separated and revealed by means of autoradiography is counted using a thin film argonmethane radioactivity analyzer (Berthold). The results are expressed as percentages of the radioactivity of the total lipids neosynthesized and deposited on the TLC.

1.5) Treatment of the Data

The groups of data (control group and treated groups) are compared by means of a one-factor analysis of variance (Anova 1, p<0.05), followed by a Dunnett test.

2) Results

After incubating overnight in the presence of the human skin disks, the test compositions and the reference compositions have no significant effect on the neosynthesis of the total epidermal lipids (table 3.1). On the other hand, they appreciably modify the proportion of the various epidermal lipids in this total:

EGF at 10 ng/ml reduced the neosynthesis of cholesteryl sulfate by 46% and increased the neosynthesis of ceramide 2 by 55% (table 3.2);

lactic acid increases the neosynthesis of the cerebrosides by a factor of 1.59 (table 3.2);

composition 1.1 increases the respective neosynthesis of ceramides 1 and 2 by a factor of 2.26 and 4.61, and the neosynthesis of cholesterol by a factor of 5.04. It reduces the neosynthesis of the tri- and diglycerides by 73% (table 3.3);

composition 1.2 increases the neosynthesis of cholesteryl sulfate by a factor of 1.32, the respective neosynthesis of ceramides 1 and 2 by a factor of 2.47 and 2.51, and the neosynthesis of cholesterol by a factor of 4.62. It reduces the neosynthesis of the tri- and diglycerides by 77% (table 3.2);

composition 1.3 increases the neosynthesis of cholesteryl sulfate by a factor of 1.24, the respective neosynthesis of ceramides 1 and 2 by a factor of 1.59 and 3.66; and the neosynthesis of cholesterol by a factor of 4.14, It reduces the neosynthesis of the tri- and diglycerides by 84% (table 3.2);

the placebo composition reduces the neosynthesis of the tri- and diglycerides by 59% (table 3.3) without causing a significant increase in the various epidermal lipids analyzed.

In conclusion, under the experimental conditions adopted, compositions 1.1, 1.2, 1.3 and placebo have no significant effect on the neosynthesis of the total epidermal lipids.

On the other hand, they significantly modify the proportion of the various classes of epidermal lipids separated by thin layer chromatography in the total.

They reduce the neosynthesis of the tri- and diglycerides to the benefit of the other epidermal lipids:

Composition 1.1 increases the neosynthesis of cholesterol (without modifying the neosynthesis of cholesteryl sulfate) and the neosynthesis of the ceramides.

Compositions 1.2 and 1.3 increase the neosynthesis of cholesteryl sulfate and cholesterol, and the neo-synthesis of the ceramides.

The placebo composition does not bring about a significant increase in the various epidermal lipids analyzed.

3) Tables of Results

TABLE 3.1

Effect of compositions 1.1, 1.2, 1.3 and placebo and also of EGF and of a cosmetic formulation containing lactic acid on the neosynthesis of the total epidermal lipids in disks of whole human skin, after incubation for 18 hours

| Control | EGF 10 ng/ml | Lactic acid | Composition 1.2 | Composition 1.3 | Composition 1.1 | Placebo composition |
|---|---|---|---|---|---|---|
| 4183.35 | 3104.63 | 1864.31 | 2479.26 | 3646.42 | 873.10 | 1506.12 |
| 4407.89 | 5043.66 | 4919.12 | 3858.70 | 5255.70 | 3726.00 | 4154.88 |
| 3691.69 | 3606.76 | 4027.67 | 6571.13 | 3900.53 | 3802.63 | 4429.96 |
| 1062.72 | 4565.02 | 1076.21 | 2457.78 | 3209.16 | 905.55 | 2373.94 |
| 3336.41 | 4080.02 | 2971.83 | 3841.72 | 4002.95 | 2326.82 | 3116.23 |
| +/− | +/− | +/− | +/− | +/− | +/− | +/− |
| 1545.02 | 883.02 | 1800.62 | 1934.04 | 882.63 | 1660.22 | 1408.09 |
| *100* | *122* | *89* | *115* | *120* | *70* | *93* |

The results are expressed in cpm/mg of epidermis

In bold: mean and standard deviation

In italics: percentage of the control group

*: mean significantly different from the control group ($p < 0.05$)

TABLE 3.2

Effect of compositions 1.2 and 1.3 and also of EGF and of a cosmetic formulation containing lactic acid on the neosynthesis of the polar lipids, of cholesteryl sulfate, of the cerebrosides, of ceramides 1 and 2, of cholesterol and of the tri- + diglycerides in disks of whole human skin, after incubation for 18 hours

| Product | Polar lipids | Cholesteryl sulfate | Cerebrosides | Ceramide 1 | Ceramide 2 | Cholesterol | Tri- + di-glycerides |
|---|---|---|---|---|---|---|---|
| Control | 28.94 | 6.04 | 1.89 | 2.03 | 2.03 | 8.23 | 50.83 |
|  | 24.96 | 4.80 | 2.08 | 2.67 | 2.07 | 5.04 | 53.76 |
|  | 31.74 | 6.26 | 4.02 | 2.71 | 2.15 | 7.89 | 45.23 |
|  | 42.90 | 5.12 | 4.44 | 1.67 | 1.47 | 5.61 | 38.84 |
|  | 32.14 | 5.56 | 3.11 | 2.27 | 1.93 | 6.69 | 47.17 |
|  | +/− | +/− | +/− | +/− | +/− | +/− | +/− |
|  | 7.70 | 0.71 | 1.31 | 0.51 | 0.31 | 1.60 | 6.58 |
|  | 100 | 100 | 100 | 100 | 100 | 100 | 100 |
| EGF 10 ng/ml | 57.27 | 2.31 | 2.87 | 2.02 | 3.81 | 7.07 | 42.67 |
|  | 34.42 | 3.69 | 3.82 | 1.41 | 2.38 | 9.46 | 44.82 |
|  | 27.69 | 3.44 | 4.77 | 3.41 | 2.74 | 7.86 | 50.08 |
|  | 33.53 | 2.57 | 4.02 | 4.02 | 3.05 | 9.99 | 42.83 |
|  | 38.23 | 3.00* | 3.87 | 2.72 | 3.00* | 8.60 | 45.10 |
|  | +/− | +/− | +/− | +/− | +/− | +/− | +/− |
|  | 13.04 | 0.67 | 0.78 | 1.21 | 0.61 | 1.36 | 3.46 |
|  | 119 | 54 | 125 | 120 | 155 | 128 | 96 |
| Lactic acid | 49.20 | 4.07 | 4.46 | 2.37 | 1.70 | 7.77 | 33.43 |
|  | 33.04 | 4.16 | 4.54 | 2.64 | 3.32 | 9.72 | 42.58 |
|  | 64.49 | 5.90 | 6.07 | 2.94 | 2.57 | 8.07 | 31.95 |
|  | 53.51 | 4.25 | 4.68 | 2.58 | 1.44 | 8.67 | 24.86 |
|  | 50.06 | 4.60 | 4.94* | 2.63 | 2.26 | 8.56 | 33.21 |
|  | +/− | +/− | +/− | +/− | +/− | +/− | +/− |
|  | 13.05 | 0.87 | 0.76 | 0.24 | 0.86 | 0.86 | 7.28 |
|  | 156 | 83 | 159 | 116 | 117 | 128 | 70 |
| Composition 1.2 | 24.57 | 6.89 | 4.41 | 2.78 | 6.86 | 44.35 | 10.13 |
|  | 28.71 | 8.34 | 5.91 | 5.94 | 3.34 | 35.04 | 12.72 |
|  | 33.09 | 6.86 | 4.02 | 4.55 | 4.79 | 36.97 | 9.72 |
|  | 35.78 | 7.35 | 7.76 | 9.20 | 4.37 | 34.01 | 11.52 |
|  | 30.54 | 7.36* | 5.53 | 5.62* | 4.84* | 37.59* | 11.02* |
|  | +/− | +/− | +/− | +/− | +/− | +/− | +/− |
|  | 4.93 | 0.69 | 1.70 | 2.72 | 1.48 | 4.67 | 1.37 |
|  | 95 | 132 | 178 | 247 | 251 | 562 | 23 |
| Composition 1.3 | 38.88 | 6.23 | 6.23 | 3.20 | 8.92 | 28.63 | 7.92 |
|  | 43.70 | 8.25 | 4.55 | 3.51 | 7.25 | 24.34 | 8.41 |
|  | 37.70 | 6.88 | 3.97 | 3.52 | 6.69 | 33.55 | 7.68 |
|  | 47.94 | 6.15 | 6.13 | 4.24 | 5.40 | 24.30 | 5.85 |
|  | 42.06 | 6.88* | 5.22 | 3.62* | 7.07* | 27.71* | 7.47* |

TABLE 3.2-continued

Effect of compositions 1.2 and 1.3 and also of EGF and of a cosmetic formulation containing lactic acid on the neosynthesis of the polar lipids, of cholesteryl sulfate, of the cerebrosides, of ceramides 1 and 2, of cholesterol and of the tri- + diglycerides in disks of whole human skin, after incubation for 18 hours

| Product | Polar lipids | Cholesteryl sulfate | Cerebrosides | Ceramide 1 | Ceramide 2 | Cholesterol | Tri- + di-glycerides |
|---|---|---|---|---|---|---|---|
| | +/− | +/− | +/− | +/− | +/− | +/− | +/− |
| | 4.70 | 0.97 | 1.13 | 0.44 | 1.46 | 4.39 | 1.12 |
| | *131* | *124* | *168* | *159* | *366* | *414* | *16* |

The results are expressed as a percentage of the radiolabeled total lipids applied onto the TLC.
In bold: mean and standard deviation
In italics: percentage of the control group
+: mean significantly different from the control group ($p < 0.05$)

TABLE 3.3

Effect of compositions 1.1 and placebo on the neosynthesis of the polar lipids, of cholesteryl sulfate, of the cerebrosides, of ceramides 1 and 2, of cholesterol and of tri- + diglycerides in disks of whole human skin, after incubation for 18 hours

| Product | Polar lipids | Cholesteryl sulfate | Cerebrosides | Ceramide 1 | Ceramide 2 | Cholesterol | Tri- + diglycerides |
|---|---|---|---|---|---|---|---|
| Control | 28.94 | 6.04 | 1.89 | 2.03 | 2.03 | 8.23 | 50.83 |
| | 24.96 | 4.80 | 2.08 | 2.67 | 2.07 | 5.04 | 53.76 |
| | 31.74 | 6.26 | 4.02 | 2.71 | 2.15 | 7.89 | 45.23 |
| | 42.90 | 5.12 | 4.44 | 1.67 | 1.47 | 5.61 | 38.84 |
| | 32.14 | 5.56 | 3.11 | 2.27 | 1.93 | 6.69 | 47.17 |
| | +/− | +/− | +/− | +/− | +/− | +/− | +/− |
| | 7.70 | 0.71 | 1.31 | 0.51 | 0.31 | 1.60 | 6.58 |
| | *100* | *100* | *100* | *100* | *100* | *100* | *100* |
| Composition 1.1 | 37.24 | 6.43 | 4.35 | 5.12 | 8.38 | 32.19 | 16.28 |
| | 32.48 | 4.83 | 5.45 | 4.22 | 7.77 | 32.51 | 12.74 |
| | 31.92 | 3.81 | 5.68 | 5.43 | 8.06 | 32.23 | 10.86 |
| | 25.87 | 4.41 | 4.49 | 5.75 | 11:37 | 38.00 | 10.11 |
| | 31.88 | 4.87 | 4.99 | 5.13* | 8.90* | 33.73* | 12.50* |
| | +/− | +/− | +/− | +/− | +/− | +/− | +/− |
| | 4.66 | 1.12 | 0.67 | 0.66 | 1.67 | 2.85 | 2.75 |
| | *99* | *88* | *161* | *226* | *461* | *504* | *26* |
| Placebo composition | 73.67 | 9.27 | 7.69 | 2.44 | 2.05 | 3.03 | 18.60 |
| | 58.70 | 11.03 | 7.60 | 2.51 | 3.39 | 3.71 | 13.07 |
| | 55.90 | 6.63 | 3.71 | 4.21 | 3.67 | 8.66 | 17.20 |
| | 63.39 | 5.69 | 4.48 | 4.17 | 3.35 | 4.93 | 27.98 |
| | 62.92 | 8.16 | 5.87 | 3.33 | 3.12 | 5.08 | 19.21* |
| | +/− | +/− | +/− | +/− | +/− | +/− | +/− |
| | 7.81 | 2.44 | 2.07 | 0.99 | 0.72 | 2.51 | 6.30 |
| | *196* | *147* | *189* | *147* | *161* | *76* | *41* |

The results are expressed as a percentage of the radiolabeled total lipids applied onto the TLC.
In bold: mean and standard deviation
In italics: percentage of the control group
+: mean signficantly different from the control group ($p < 0.05$)

EXAMPLE 3

Composition of a Cream for Atopic Skin

| INCI formulation | % |
|---|---|
| Water qs | 100 |
| Glycerol | 15 |
| Petrolatum | 2 |
| Hydrogenated palm kernel oil | 5 |
| Caprylic/capric triglycerides | 5 |
| Cyolomethicone | 1 |
| Sucrose distearate | 4 |
| Dextrin | 3 |
| Sunflower (Helianthus annuus) seed oil unsaponifiables (1) | 1 |
| Squalane | 2 |
| Candelilla (Euphorbia cerifera) wax | 1 |
| Sucrose stearate | 2 |
| Oat (Avena sativa) flour | 1 |
| Dimethiconol | 0.2 |
| Methylparaben | 0.4 |
| Propylparaben | 0.3 |
| Xanthan gum | 0.2 |
| Ceramide 3 | 0.2 |
| Total: | 100% |

(1): Sunflower oil distillate 1 of example 1

EXAMPLE 4

Composition of a Bath Oil for Atopic Skin

| INCI formulation | % |
| --- | --- |
| Sunflower (Helianthus annulus) seed oil qs | 100 |
| Octyl cocoate | 15 |
| Sweet almond (Prunus amygdalus dulcis) oil | 15 |
| Mineral oil | 1 |
| PEG-6 isostearate | 5 |
| Sunflower (Helianthus annuus) seed oil unsaponifiables (1) | 60 |
| Chamomile (Anthemis nobilis) oil | 5 |
| Propylene glycol dipelargonate | 1 |
| Lecithin | 1 |
| Laureth-2 | 0.5 |
| Tocopherol | 0.5 |
| Ascorbyl palmitate | 0.06 |
| Total: | 100% |

(1): Sunflower oil distillate 1 of example 1

EXAMPLE 5

Clinical Study to Evaluate the Care Effect of Composition 1.1 of Example 1 and Checking of its Satisfactory Local Skin Tolerance, Under Dermatological Control, after Single and Repeated Applications for 4 Weeks, on an "Atopic" Adult Volunteer 1) Materials and Method
1.1 Aim of the Study The aim is firstly to evaluate the care effect of a cosmetic product, by various biometrological measurements combined with clinical evaluations, and secondly to check their satisfactory local skin tolerance, after single and repeated cutaneous applications for 4 weeks, on an "atopic" adult volunteer with very dry and squamous body skin.

1.2 Relevance of the Test

"Double-blind" evaluations, based on:
the principles of electrical conductivity of the skin, widely described for determining the state of moisturization of the upper layers of the epidermis (Tagami H. et al., 1980; Korstanje et al., 1992);
the principle of photometry (sebumetric measurements), for evaluating the relipidizing effect of a cosmetic product;
analysis by optical microscopy of surface "biopsies", performed by stripping, using cyanoacrylate adhesive, making it possible to determine the effect of a cosmetic product on the "MicroDepression Network" (MDN);
a clinical evaluation by the Study Director, self-evaluation by the panelist and a questionnaire.

1.3 Inclusion Criteria

"Atopic" volunteer with dry to very dry and slightly squamous body skin (dryness score $\geq 5$ on a scale from 1 to 9).

1.4 Population Studied

18 "atopic" adult female volunteers (or 20 for the kinetics), from 20 to 28 years old, with dry or very dry skin (2 dropouts from the study, not associated with the applications).

1.5 Modes of Application

Single application: 0.07 ml of product, i.e. 2 µl/cm², on one or two areas of about 35 cm² delimited on the skin of the right or left leg, according to a chance randomization. A control area was also delimited for each measurement type (corneometry and sebumetry).

Repeated uses: twice a day, under the normal conditions for use, for 4 consecutive weeks, by the volunteer himself at his home, to half the body.

1.6 Methodology

Single application: measurement of the electrical capacitance using a Cornéométre™ (Courage+Khazaka electronic GmbH, Germany) and of the initial level of surface skin lipids using a Sébumètre™ SM 810 PC (Courage and Khazaka) on areas treated with the test product (moisturization kinetics only), and also on an untreated control area (one control area per measurement type) before and then 1, 2, 3 and 24 hours approximately after applying the products.

Repeated uses:

measurement of the electrical capacitance using a Cornéométre™ (Courage+Khazaka electronic GmbH, Germany) on areas treated with the test product before, and then after the 4 weeks of use of the product;

production of surface "biopsies" by stripping, followed by analysis by optical microscopy, on semi-structured linear scales of 12 cm, taking into account the cleanliness of the Microdepression Network and the surface appearance, before and then after the 4 weeks of applications;

clinical evaluation by the Study Investigator and self-evaluation by the panelists of the "dryness", the "roughness" and the "desquamation" of the skin, on the basis of clinical scores or of analogue visual scales, at the same times as previously;

assessment of the local skin tolerance of the product by the Dermatologist, after the 4 weeks of use;

temperature and relative humidity regulated and checked at each testing time (T°=22±2° C. and RH=50±5%).

1.7 Statistics

Instrumental measurements (corneometry and sebumetry): ANOVA and multiple-comparisons test (p<0.05) relating to the absolute values and to the differences ($\Delta$ Tx−T0).

MDN, analogue scales and clinical scores: Wilcoxon test in paired series ("two-tail", p<0.05).

Calculation of the percentages of variation the parameters evaluated during the study.

2) Results 2.1 Effect on the Level of Surface Skin Lipids after Single Application (Sébumètre™)

A statistically significant increase in the level of surface skin lipids relative to the initial measurements and to the values recorded on the control area, 1 and then 2 and 3 hours approximately after the first application, are found, reflecting an immediate marked relipidizing effect, not revealed approximately 24 hours after the application (reflecting a total absorption of composition 1.1, without the presence of a residual greasy film on the surface of the skin).

2.2 Effect on the Degree of Moisturization of the Upper Layers of the Epidermis after Single and Repeated Applications (Cornéométre™).

After single application (n=20)

A statistically significant increase in the electrical capacitance is found relative to the initial measurements and to the measurements recorded on the control area, 1 and then 2, 3 and 24 hours approximately after the first application of composition 1.1.

After 4 weeks of repeated use (n=18)

A statistically significant increase in the electrical capacitance relative to the initial measurements is found.

TABLE 5.1

| GAINS IN MOISTURIZATION | Control area | COMPOSITION 1.1 (EXAMPLE 1) |
|---|---|---|
| T 1 hour | +0.0% | +48.6%° |
| T 2 hours | +1.0% | +58.7%° |
| T 3 hours | +0.5% | +64.4%° |
| T 24 hours | +2.9% | +34.2%° |
| T 4 weeks |  | +22.4%° |

°: statistically significant increase in comparison with the untreated control area 2.3 Effect on the Microdepression Network
(analysis by optical microscopy of surface "biopsies": 5-12 cm semi-structured linear scales)
A statistically significant restructuring of the MicroDepression Network is found, after 4 weeks of application.

TABLE 5.2

|  | COMPOSITION 1.1 (EXAMPLE 1) |
|---|---|
| Microrelief | +10% |
| Surface appearance | +52% |

2.4 Clinical Evaluation by the Study Director
(g-point clinical scores)
A statistically significant variation in the following judgement criteria is observed, after 4 weeks of application:

TABLE 5.3

|  | COMPOSITION 1.1 (EXAMPLE 1) |
|---|---|
| Skin dryness | −54% (p = 0.0002) |
| Skin roughness | −52% (p = 0.0002) |
| Desquamation | −54% (p = 0.0004) |

2.5 Self-Evaluation by the Volunteers
(10-point analogue visual scales)
A statistically significant variation in the following judgement criteria is observed, after 4 weeks of application:

TABLE 5.4

|  | COMPOSITION 1.1 (EXAMPLE 1) |
|---|---|
| Skin dryness | −60% (p = 0.0002) |
| Skin roughness | −55% (p = 0.0002) |
| Desquamation | −60% (p = 0.0002) |

3) Conclusion

In conclusion, the single application to the skin of composition 1.1 to 20 "atopic" female adult volunteers with dry to very dry skin, in comparison with an untreated control area (under double-blind conditions), resulted in:
a statistically significant effect on the content of surface skin lipids (photometric measurements), in comparison with an untreated control area, reflecting a marked immediate relipidizing effect, not revealed 24 hours approximately after the application, reflecting a total absorption of the product, without the presence of a residual greasy film on the surface of the skin;
a marked effect on the degree of moisturization of the upper layers of the epidermis (electrical capacitance measurements), 1, 2, 3 and 24 hours approximately after the application, reflecting an excellent remanence.

The repeated applications, twice a day for 4 consecutive weeks, under the normal conditions for use, by a panel of 18 adult female individuals, moreover, resulted in:
a statistically significant effect on the degree of moisturization of the upper layers of the epidermis;
a statistically significant restructuring of the microdepression network;
a statistically significant improvement in the appearance of the skin (dryness, roughness and desquamation).

A positive judgement was also given by the majority of the panelists for the efficacy of composition 1.1 as a "care cream for dry skin", and also for its cosmetic qualities.

The applications of the studied composition 1.1 were found, moreover, to be very well tolerated.

This set of results thus makes it possible to justify, for composition 1.1, the following properties:
an immediate relipidizing effect,
an immediate and long lasting moisturizing effect on the upper layers of the epidermis,
an improvement in the appearance of the skin, and
a tolerance and efficacy tested under dermatological monitoring.

The invention claimed is:

1. A method of treating a skin condition of a subject, wherein a skin of said subject has a quantity of skin lipids, comprising:
administering to a subject in need thereof an effective amount of a composition comprising at least one plant oil product selected from the group consisting of oil distillate of sunflower oil and unsaponifiable materials from sunflower oil,
wherein said quantity of skin lipids increases by neosynthesis after administration of said composition, wherein said skin lipids that increase after administration are selected from the group consisting of cholesterol, ceramide 1, and ceramide 2; and
wherein said skin condition is selected from the group consisting of atopic dermatitis, irritated skin, reactive skin, sensitive skin, dry skin, pruritus, ichtyosis, acne, xerosis, atopic dermatitis, cutaneous desquamation, skin subjected to actinic radiation, or skin subjected to ultraviolet (UV) radiation.

2. The method of claim 1 wherein said subject has an epidermal skin barrier and said skin lipids are lipids of said epidermal skin barrier.

3. The method of claim 1 wherein said 1 plant oil product is present in an amount of between 0.01% and 100% by weight relative to the total weight of the composition.

4. The method of claim 1 wherein said unsaponifiable materials are present in said plant oil product in an amount of 5 to 50% by total weight of said plant oil product.

5. The method of claim 4 wherein said unsaponifiable materials are present in said plant oil product in an amount of 10 to 20% by total weight of said plant oil product.

6. The method of claim 1 wherein said composition is administered topically, orally, enterally or parenterally.

7. The method of claim 1 wherein said composition is applied to the skin, the neighboring mucous membranes and/or the integuments.

8. The method of claim 1 wherein said composition is administered to treat skin that is sensitive, irritated or reactive.

9. The method of claim 1 wherein said composition is a cosmetic, pharmaceutical or dermatological composition.

10. The method of claim 9 wherein said cosmetic, pharmaceutical or dermatological composition comprises an oily solution, a water-in-oil emulsion, an oil-in-water emulsion, a micro-emulsion, an oily gel, an anhydrous gel or a dispersion of vesicles, microcapsules or microparticles.

11. A method of treating a skin condition of a subject, wherein a skin of said subject has a quantity of skin lipids, comprising:
 administering to a subject in need thereof an effective amount of a composition comprising at least one plant oil product selected from the group consisting of oil distillate of sunflower oil and unsaponifiable materials from sunflower oil,
 wherein said quantity of skin lipids increases by neosynthesis after administration of said composition, wherein said skin lipids that increase after administration are selected from the group consisting of cholesterol, and ceramides; and
 wherein said skin condition is selected from the group consisting of atopic dermatitis, irritated skin, reactive skin, sensitive skin, dry skin, pruritus, ichtyosis, acne, xerosis, atopic dermatitis, cutaneous desquamation, skin subjected to actinic radiation, or skin subjected to ultraviolet radiation.

\* \* \* \* \*

UNITED STATES PATENT AND TRADEMARK OFFICE
CERTIFICATE OF CORRECTION

PATENT NO. : 8,147,883 B1
APPLICATION NO. : 10/088851
DATED : April 3, 2012
INVENTOR(S) : Philippe Msika et al.

Page 1 of 1

It is certified that error appears in the above-identified patent and that said Letters Patent is hereby corrected as shown below:

In the Specification
    Column 1, line 14, delete the "," after the word --skin--.
    Column 1, line 22, delete the "," after the word --for--.
    Column 1, line 46, "desirable to able" should read --desirable to be able--.
    Column 2, line 32, "late are rich" should read --late is rich--.
    Column 3, line 43, delete the "," after the word --fatty--.
    Column 4, line 15, delete the "," after the word --from--.
    Column 6, line 9, delete the "," after the word --makes--.
    Column 11, line 1, delete the "," after the word --human--.
    Column 11, line 10, "(subject I0129)" should read --(subject 10129)--.
    Column 12, line 3, "3 700" should read --3700--.
    Column 15, Table 3.2, Ceramide 2, +/- "1.46" should read --11.46--.
    Column 18, line 36, "comparisons test" should read --comparisons tests--.
    Column 18, line 40, "variation the parameters" should read --variation of the parameters--.

In the Claims
    Column 20, line 50, "wherein said 1 plant" should read --wherein said plant--.
    Column 22, line 4, delete the "," after the word --cholesterol--.

Signed and Sealed this
Twenty-third Day of July, 2013

Teresa Stanek Rea
*Acting Director of the United States Patent and Trademark Office*